United States Patent [19]
Lakiss-Smith

[11] Patent Number: 5,454,799
[45] Date of Patent: Oct. 3, 1995

[54] NAPPY

[76] Inventor: Rosemarie Lakiss-Smith, 5 Richards Avenue, Surry Hills, New South Wales 2010, Australia

[21] Appl. No.: 158,728

[22] Filed: Nov. 29, 1993

Related U.S. Application Data

[63] Continuation of Ser. No. 777,348, Jan. 31, 1992, abandoned.

[30]    Foreign Application Priority Data

Jun. 9, 1989 [AU] Australia ............................ PJ4642
Jun. 26, 1989 [AU] Australia ............................ PJ4890

[51] Int. Cl.⁶ .......................... A61F 13/15; A61F 13/20
[52] U.S. Cl. ...................... 604/358; 604/378; 604/366; 604/370; 604/385.1
[58] Field of Search ........................ 604/358, 366, 604/369, 370, 371, 373, 377–383, 385.1, 385.2, 393, 396

[56]          References Cited

U.S. PATENT DOCUMENTS

| | | | |
|---|---|---|---|
| 4,402,690 | 9/1983 | Redfern. | |
| 4,516,975 | 5/1985 | Mitchell. | |
| 4,573,987 | 3/1986 | Lamb, Jr. | 604/378 |
| 4,798,603 | 1/1989 | Meyer. | |
| 5,306,267 | 4/1994 | Hahn et al. | 604/358 |
| 5,342,340 | 8/1994 | Kichefski et al. | 604/358 |
| 5,360,421 | 11/1994 | Revelle | 604/371 |
| 5,403,303 | 4/1995 | Beplate | 604/358 |

FOREIGN PATENT DOCUMENTS

| | | |
|---|---|---|
| 125203 | 8/1947 | Australia. |
| 122803 | 10/1984 | European Pat. Off.. |
| 2164542 | 3/1986 | United Kingdom. |
| 2194878 | 3/1988 | United Kingdom. |

Primary Examiner—Jerome L. Kruter
Assistant Examiner—P. Zuttarelli
Attorney, Agent, or Firm—Ladas & Parry

[57]          ABSTRACT

A washable nappy (10) having a rear portion (11) which tapers towards a crotch portion (12) which then joins to a front portion (13). Fasteners are used to secure the rear portion (11) to the front portion (13) so that the nappy is retained in position. The nappy is of a laminated structure having an outer layer formed of plush cotton toweling and a co-terminus inner layer formed of brush cotton. An intermediate layer is formed of 100% bonded polyester which covers at least the crotch portion and aids in transporting moisture from the inner layer to the outer layer.

3 Claims, 1 Drawing Sheet

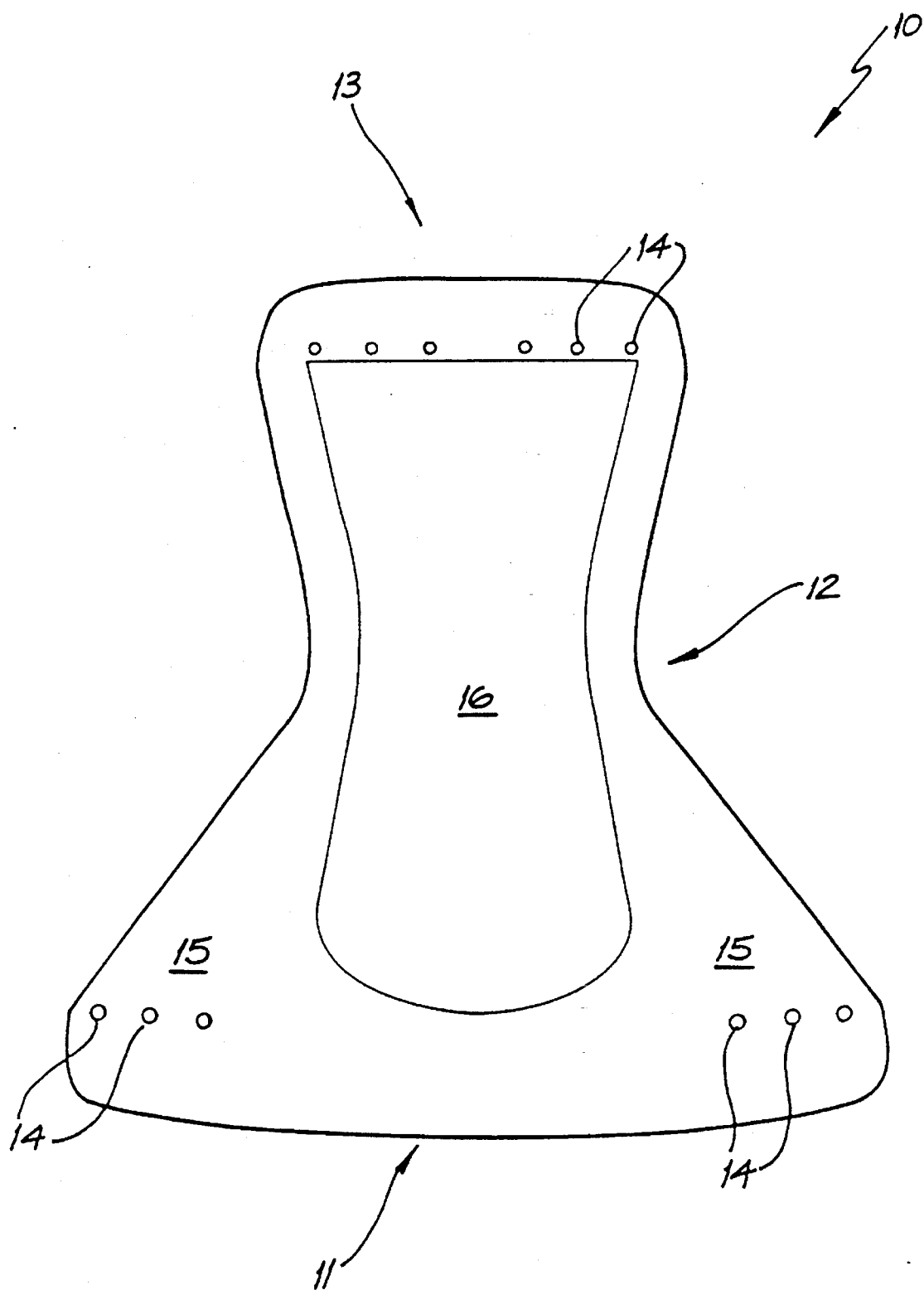

NAPPY

This is a continuation of application(s) Ser. No. 07/777,348 filed on Jan. 31, 1992, now abandoned, and International Application PCT/AU90/00257 filed on Jun. 8, 1990 and which designated the U.S.

TECHNICAL FIELD

The present invention relates to re-usable cloth nappies (diapers).

BACKGROUND ART

Nappies traditionally consisted of a square of cotton material (toweling) which was folded and secured in position by means of a safety pin. These traditional nappies have suffered from the disadvantage that the wet cloth stays in contact with the baby. A still further disadvantage is that they are not shaped to fit the baby and must be folded in an awkward manner before being applied.

More recently disposable nappies (disposable diapers) have become popular. They are particularly well adapted for maintaining the baby However a disadvantage of these known disposable nappies is the environmental problem in respect of their manufacture and disposal.

OBJECT OF THE INVENTION

It is the object of the present invention to overcome or substantially ameliorate the above disadvantages.

DISCLOSURE OF INVENTION

There is disclosed herein a washable happy (diaper), said nappy being shaped to fit about the legs and waist of a user by having a rear tapering forward to a crotch portion, and a front portion extending from the crotch portion, and wherein said happy is of a laminated structure so as to have an outermost layer of absorbent fabric material, an innermost layer generally co-terminus with respect to said outer layer and also formed of absorbent fabric material, and an intermediate layer located at least at said crotch portion, said intermediate layer being formed of synthetic material so as to aid in the transfer of moisture from the inner layer to the outer layer.

Preferably the above washable happy would have the inner layer formed of soft brush cotton or flannelette. The outer layer is preferably formed of plush cotton toweling. The inner layer is formed of 100% bonded polyester fibre.

BRIEF DESCRIPTION OF THE DRAWING

In the accompanying drawing there is schematically depicted in view a washable nappy (diaper).

DESCRIPTION OF THE PREFERRED EMBODIMENT

In the accompanying drawing there is schematically depicted a washable nappy 10. The nappy 10 has a rear portion 11 tapering forward to a crotch portion 12. Extending from the crotch portion 12 is a front portion 13. Secured to the rear portion 11 and front portion 13 are releasable fasteners 14 which engage to secure the nappy in position. For example, the fasteners 14 could be "press tabs". The nappy 10 is shaped so that the side extensions 15 pass around the outer surfaces of the leg of the user to engage the front portion 13.

The happy 10 is of a laminated structure, with the outer layer being formed of plush cotton toweling. The happy 10 has an inner layer which is generally co-terminus with respect to the outer layer which inner layer is formed of brush cotton or flannelette.

Sandwiched between the inner and outer layers is an intermediate layer 16 formed of 100% bonded polyester. The inner layer 16 covers at least the crotch portion 12 and extends partly toward the front and rear portions 11 and 13.

In use of the above described nappy 10, the inner layer (flannelette) provides a soft surface to abut the baby's skin. The intermediate layer 16 aids in transferring moisture from the inner layer to the outer layer. The outer layer being formed of toweling provides for the absorbtion of the moisture.

I claim:

1. A washable diaper, said diaper being shaped to fit around a user's legs and waist by having a rear portion tapering toward a crotch portion, and a front portion extending from the crotch portion, with the front portion and the rear portion being securable to retain the diaper extending around the waist of the user, and wherein said crotch portion consists of a laminated structure comprising three, layers, said layers being an outermost layer which is that layer to be positioned most remote from the user's skin, and an innermost layer being generally co-terminus with respect to said outermost layer and formed of brushed cotton or flannelette, and an intermediate layer, said intermediate layer being formed of synthetic material so as to aid in transfer of moisture from the innermost layer to the outermost layer by contacting said innermost layer and said outermost layer.

2. A washable diaper, said diaper being shaped to fit about a user's legs and waist by having a rear portion tapering forward to a crotch portion, and a front portion extending from the crotch portion, and wherein said diaper has a plurality of layers so as to be of a laminated structure and providing an outermost layer which is that layer to be positioned most remote from the user's skin and an innermost layer being generally co-terminus with respect to said outermost layer and formed of brushed cotton or flannelette, and an intermediate layer located at least at said crotch portion, said intermediate layer being formed of 100% bonded polyester so as to aid in transfer of moisture from the innermost layer to the outermost layer, by contacting said innermost layer and said outermost layer.

3. A washable diaper, comprising:

a first, innermost layer of one of brushed cotton and flannelette for location on a user's skin;

a second, outermost layer of plush cotton towelling on one side of the first layer for an outermost location remote from the user's skin, the first and second layers being generally co-terminurs about peripheries of the first and second layers, the peripheries of the first and second layers defining a rear portion of the first and second layers that tapers in one, forward direction to a crotch portion of the first and second layers and a front portion of the first and second layers that extends in the one, forward direction from the crotch portion; and an intermediate layer in contact with the first and second layers at least at a portion of the crotch portion, the intermediate layer being formed of about 100% bonded polyester for aiding transfer of moisture from the first layer to the second layer.

* * * * *